United States Patent [19]

Carter

[11] 3,979,475

[45] Sept. 7, 1976

[54] RECOVERY OF HF AND ETHYL FLUORIDE FROM ALKYLATION OF ISOPARAFFIN WITH OLEFINS IN PRESENCE OF HF CATALYST

[75] Inventor: Cecil O. Carter, Wann, Okla.

[73] Assignee: Phillips Petroleum Company, Bartlesville, Okla.

[22] Filed: Dec. 10, 1974

[21] Appl. No.: 531,490

[52] U.S. Cl.......................... 260/683.42; 260/683.51
[51] Int. Cl.².......................................... C07C 3/54
[58] Field of Search.................. 260/683.51, 683.48, 260/683.42

[56] References Cited
UNITED STATES PATENTS

| | | |
|---|---|---|
| 3,751,517 | 8/1973 | Hutson, Jr. et al............. 260/683.51 |
| 3,763,265 | 10/1973 | Hutson, Jr. et al............. 260/683.48 |
| 3,767,727 | 10/1973 | Chapman...................... 260/683.48 |
| 3,864,423 | 2/1975 | Chapman...................... 260/683.51 |
| 3,911,044 | 10/1975 | Carter............................. 260/683.48 |

Primary Examiner—G. J. Crasanakis

[57] ABSTRACT

Lean HF is used to extract ethyl fluoride from depropanizer overhead by steps including contacting liquid propane containing ethyl fluoride with lean HF thus taking ethyl fluoride into the HF phase, contacting vent gas from the depropanizer overhead with lean HF thus taking into the HF ethyl fluoride from the vent gases, and passing thus enriched HF phases to an alkylation reactor thus recovering ethyl fluoride and HF acid for use in the alkylation reaction. There are recovered a propane yield stream substantially free from ethyl fluoride as well as a vent gas also substantially free from ethyl fluoride.

4 Claims, 1 Drawing Figure

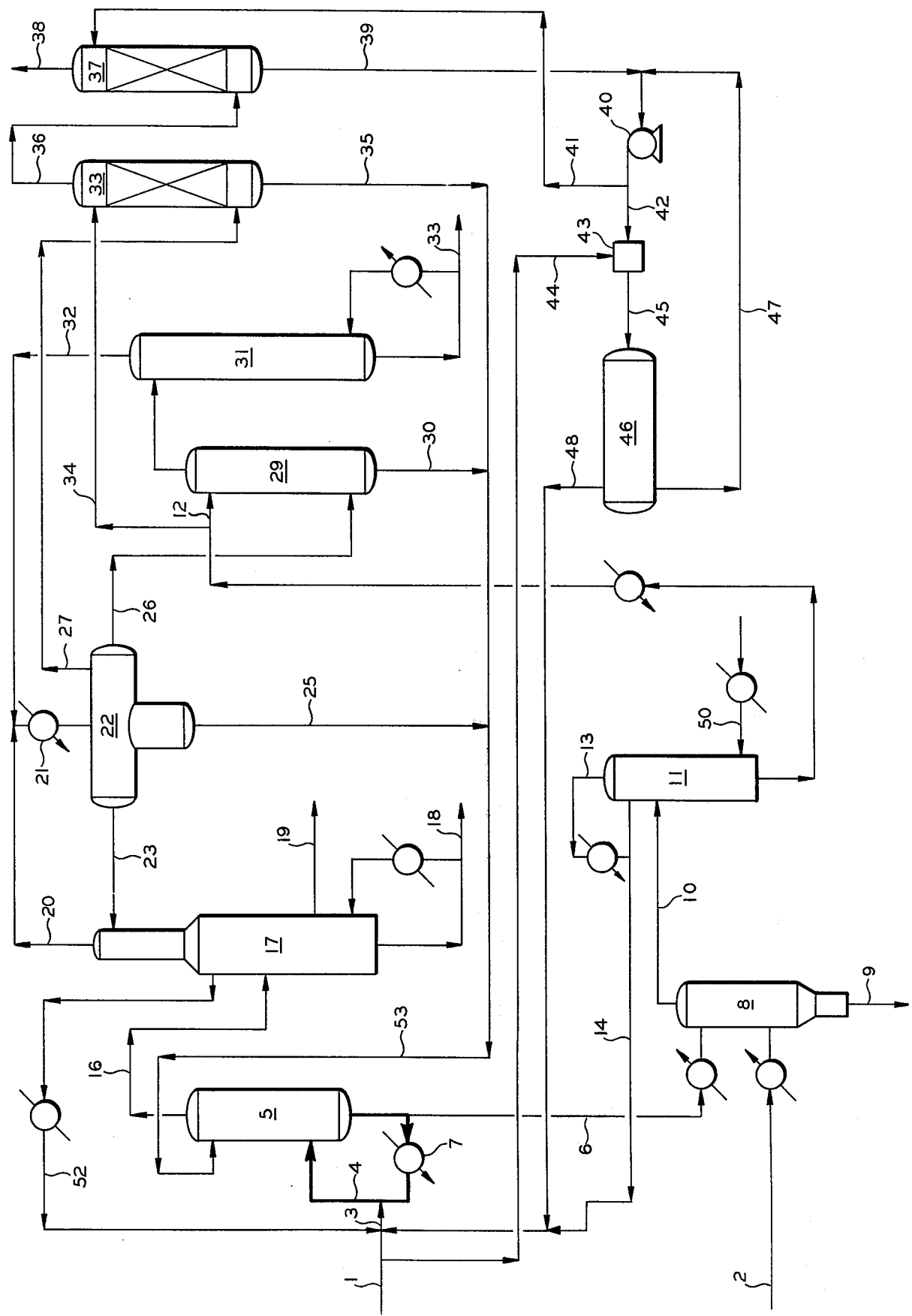

RECOVERY OF HF AND ETHYL FLUORIDE FROM ALKYLATION OF ISOPARAFFIN WITH OLEFINS IN PRESENCE OF HF CATALYST

This invention relates to alkylation of hydrocarbons. In one of its aspects, it relates to the alkylation of an isoparaffin with olefins in a reaction system in which there is present ethyl fluoride. In another of its aspects, the invention relates to the recovery of ethyl fluoride and HF from an alkylation effluent.

In one of its concepts, the invention provides a process for the recovery of ethyl fluoride from an isoparaffin-olefin alkylation reaction effluent which contains propane and ethyl fluoride by fractionation to produce a liquid fraction consisting essentially of propane containing ethyl fluoride, contacting said fraction with a lean HF acid thereby removing into the acid ethyl fluoride from the propane to recover propane from which substantial ethyl fluoride has been removed, also obtaining a gaseous propane stream containing ethyl fluoride, separately contacting the gaseous stream with a lean HF acid to remove ethyl fluoride from the gases into the HF thus obtaining gases from which substantial ethyl fluoride has been removed and which are suitable for use as a fuel, recovering thus enriched HF acid streams, and passing thus recovered streams to the alkylation reaction. Another of its concepts the invention provides steps in a method in combination and an apparatus for recovering from the propanizer overhead containing essentially propane and ethyl fluoride, the ethyl fluoride by condensing the overhead to form two phases a liquid propane phase and a vent gas phase, treating each of said phases separately with lean HF acid to absorb ethyl fluoride therefrom and recovering and returning the ethyl fluoride to the alkylation.

The shortage of fuels and the effort to reduce lead in motor fuels requires the utmost be done to obtain maximum high octane of fuels in economic manner. Thus, as the amount of lead that can be used in motor fuel is reduced to meet industry and government control levels, the provision of sufficient satisfactory octane level fuel becomes more difficult. The hydrogen fluoride alkylation of isoparaffin with olefins is well known as one skilled in the art in possession of this disclosure will understand.

It is an object of this invention to provide a process for the alkylation of isoparaffin with olefins. It is another object of this invention to provide an apparatus for the alkylation of an isoparaffin with olefins. It is a further object of this invention to provide for the recovery of ethyl fluoride which is produced in an alkylation of an isoparaffin with olefins. It is still a further object of this invention to provide a unitary or integrated process or combination of steps in which there is economically recovered ethyl fluoride and HF for reuse in an alkylation of an isoparaffin with olefins.

Other aspects, concepts, objects, and the several advantages of the invention are apparent from a study of this disclosure of the drawing and the appended claims.

According to the present invention, in an alkylation of an isoparaffin with olefins the alkylation effluent from the reaction zone is fractionated to recover therefrom, essentially, an overhead containing HF, a propane, ethyl fluoride and other hydrocarbons or gases as known in the art, upon separation of an acid phase, a propane phase, and a vent gas, the propane phase is treated with lean HF to remove ethyl fluoride therefrom, and the vent gases are treated with a lean HF to remove ethyl fluoride therefrom, thus obtaining propane from which substantial ethyl fluoride has been removed and vent gases from which substantial ethyl fluoride has been removed, the enriched HF thus obtained, from the contactings described, being passed for reuse in the alkylation in the reaction zone.

Referring now to the drawing, mixed olefin stream containing methane, ethylene, ethane, propylene, propane, some butene-2 is passed by 1 together with isobutane introduced at 2 and by 3 into riser reactor 4 wherein alkylation reaction takes place under conditions known in the art. The effluent from the alkylation riser reactor 4 is passed to a settler 5 from which most of the settled acid is recycled through heat exchanger 7 into reactor 4 and the remainder passed by 6 to rerun tower 8 from the bottom of which impurities such as catalyst soluble oils are removed at 9. Overhead 10 is passed to stripper 11 wherein ethyl fluroride is stripped from the HF, as later further described, yielding a bottom stream 12 lean in ethyl fluoride for use according to the invention as later described. Ethyl fluoride is taken overhead by 13 and 14 and returned by 14 to the alkylation operation together with acid which is recycled from 6 by way of cooler of 7 and 4, as earlier described. The hydrocarbon phase is taken from settler 5 by 16 to fractionator 17 from which alkylate is removed as bottoms 18, a normal butane stream is taken as side draw 19 and a propane rich overhead is taken off at 20 and passed by cooler condenser 21 to accumulator 22 from which some condensate is used as reflux by way of 23 to reflux tower 17. In accumultor 22, there separates an HF acid phase removed at 25, a liquid propane phase taken off at 26 and vent gases taken off at 27.

According to the invention, the liquid propane in 26 is passed to contactor 29 wherein it is contacted with lean HF acid introduced by 12. HF containing ethyl fluoride and some propane is removed as bottoms 30 and recycled via pipe 53 to reactor settler 5. The thus treated propane is passed to HF stripper 31 from which HF is taken overhead by 32, bottoms therefrom 33 being a propane product stream.

The vent gases from accumulator 22 taken off by 27 are passed to contactor 33 and therein contacted with lean HF introduced by 34 resulting in an HF of bottoms 35 containing ethyl fluoride which are returned by 35 and 53 to reactor settler 5. The overhead gases from contactor 33 are taken by 36 to contactor 37 from which a gas washed with water or HF water solution containing a preponderance of water is taken off at 38 and usable as a fuel. Bottoms 39 containing HF acid and water are passed to pump 40 for in-part recirculation by 41 to contactor 37 and in part for circulation by 42 to mixer-reactor 43 wherein there are admixed and reacted therewith 44 some or all of the mixed olefin feed to the process, the mixture being passed by 45 to phase separator 46. The contents of the reactor can be recirculated to pump 40 and thence back to the reactor by way of 47. Alkyl fluorides thus generated are passed by 48 to 3 and thence to reactor riser 4.

In the rerun operation a stripping fluid, e.g., propane is introduced by 50 to stripper 11 to recover ethyl fluoride and to form, as earlier described, the lean HF which is used in contactor 29 and in contactor 33.

According to the invention, the rerun unit differs from normal design of the usual single 25 psig fractionator which ordinarily has four foot ID × 16 trays operating with a kettle temperature of 225°F in that the second stripper 11 is included. This second stripper operates at about 25 psig contains 10 trays and has a top temperature of 120°F and a bottom temperature of about 130°F and is included so that at least some of the rerun hydrogen fluoride can be stripped with propane vapor and taken as kettle product, cooled and used as absorbent in the ethyl fluoride extraction at 29 and at 33. The amount of propane used is held at a minimum as any excess use reduced to the capacity of the unit. All of the isobutane enters via pipe 2 and acts as stripping vapor in stripper 8. The isobutane finds its way via pipes 10, 14, and 3 to alkylation reactor 4.

The conditions for the operation of reactor riser 4 are generally well known in the art. These conditions include a reactor temperature of about 90°F, an isobutaned olefin volume ratio, external, of 13 to 1 or thereabouts, an estimated water concentration in the system HF acid catalyst of the order of less than 1 percent about 0.6 weight percent and a residence time of approximately 25 seconds. The foregoing conditions are simply for disclosure purposes. As one skilled in the art knows, he must adjust his conditions for each feed stock so as to obtain optimum results. This adjustment can be made by mere routing testing. The conditions given herein do not necessarily form a part of the invention in the sense that they are necessarily critical to it.

The ethyl fluoride concentration in the system HF acid catalyst, in the operation described in the drawing, will be of the order of about 22 weight percent.

The use of ethyl fluoride as reaction improver is set forth described and claimed in Ser. No. 349,181 filed Apr. 9, 1973.

Under the conditions above discussed, there will be produced in the riser reactor an alkylate containing ethyl fluoride.

To further illustrate the invention, the streams identified in the drawing, which are helpful to a more full understanding of the invention, are set forth in the following table.

TABLE I

MATERIAL BALANCE (BBL/DAY) FOR 10,000 BBL/DAY ALKYLATE UNIT

| Component | 1 Olefin Feed | 2 Isobutane Feed | 3 Total Alkylation Reactor Charge | 14 Recycle from HF Rerun | 52 Isobutane Recycle | 48 Hydrocarbon Effluent from Fluoride Reactor | 4 Alkylation Reactor Effluent | 6 HF to Rerun |
|---|---|---|---|---|---|---|---|---|
| 1. Methane | 1,290 | | 1,290 | | | 1,290 | 1,290 | |
| 2. Ethylene | 731 | | 731 | | | 731 | | |
| 3. Ethane | 882 | | 902 | 20 | | 882 | 902 | |
| 4. Propylene | 2,377 | | 2,377 | | | 2,377 | | |
| 5. Propane | 710 | 57 | 7,599 | 1,000 | 5,889 | 710 | 16,102 | 425 |
| 6. Butenes | 2,989 | | 2,299 | | | 2,299 | | |
| 7. Isobutane | 1,399 | 5,431 | 79,261 | 7,243 | 70,619 | 1,399 | 115,472 | 1,812 |
| 8. n-Butane | 376 | 229 | 5,605 | 302 | 4,927 | 376 | 7,071 | 73 |
| 9. Ethyl Fluoride | | | 7,697 | 5,773 | 1,924 | | 13,470 | 5,773 |
| 10. Isobutyl Fluoride | | | 834 | | | | 834 | |
| 11. Alkylate | | | 122 | 122 | | | 2,443 | 122 |
| 12. HF | | | | | | | 310,604 | 15,541 |
| 13. A.S.O. | | | | | | | 7,721 | 386 |
| 14. Water | | | | | | | 6,402 | 318 |
| Total | 10,754 | 5,717 | 108,595 | 14,460 | 83,359 | 10,898 | 482,311 | 24,450 |

| Component | 16 Hydrocarbon Effluent from Reactor Settler | 18 Alkylate Product | 19 n-Butane Product | 50 Stripping Propane to Rerun | 33 Propane Product | 27 Vent Gas to EF Extractor | 36 Vent Gas from EF Extractor | 38 Vent Gas from HF Extractor |
|---|---|---|---|---|---|---|---|---|
| 1. Methane | 1,290 | | | | | 1,290 | 1,290 | 1,290 |
| 2. Ethylene | | | | | | | | |
| 3. Ethane | 902 | | | | | 902 | 902 | 882 |
| 4. Propylene | | | | | | | | |
| 5. Propane | 7,837 | | | 518 | 1,005 | 238 | 238 | 53 |
| 6. Butenes | | | | | | | | |
| 7. Isobutane | 72,431 | | 27 | | 8 | | | |
| 8. n-Butane | 5,605 | | 605 | | | | | |
| 9. Ethyl Fluoride | 7,697 | | | | | 1,848 | | |
| 10. Isobutyl Fluoride | | | | | | | | |
| 11. Alkylate | 10,000 | 10,000 | | | | | | |
| 12. HF | | | | | | | 72 | 144 |
| 13. A.S.O. | | | | | | | | |
| 14. Water | | | | | | | | |
| Total | 105,762 | 10,000 | 632 | 518 | 1,013 | 4,350 | 2,574 | 2,225 |

| Component | 12 Lean HF to EF Extractor | 34 Lean HF to Vent Gas EF Extractor | 35 Rich HF from EF Extractor | 9 Reject A.S.O. | 39 Rich Solvent from HF Extractor | 41 Lean Solvent to HF Extractor | 44 Olefin to Fluoride Reactor |
|---|---|---|---|---|---|---|---|
| 1. Methane | | | | | | | 1,290 |
| 2. Ethylene | | | | | | | 731 |
| 3. Ethane | | | 20 | | 1 | 1 | 882 |
| 4. Propylene | | | | | | | 2,377 |
| 5. Propane | 201 | 227 | 185 | | 2 | 2 | 710 |
| 6. Butenes | | | | | | | 2,989 |
| 7. Isobutane | | | | | | | 1,399 |
| 8. n-Butane | | | | | | | 376 |
| 9. Ethyl Fluoride | | | 1,848 | | | | |
| 10. Isobutyl Fluoride | | | | | 20 | 20 | |

TABLE I-continued

MATERIAL BALANCE (BBL/DAY) FOR 10,000 BBL/DAY ALKYLATE UNIT

|  |  |  |  |  |  |  |  |
|---|---|---|---|---|---|---|---|
| 11. Alkylate |  |  |  |  |  |  |  |
| 12. HF | 5,875 | 6,624 | 6,552 | 45 | 345 | 201 |  |
| 13. A.S.O. |  |  |  | 386 |  |  |  |
| 14. Water | 124 | 146 | 146 |  | 805 | 805 |  |
| Total | 6,200 | 6,997 | 8,751 | 431 | 1,174 | 1,203 | 10,754 |

Generally the method of the invention can be applied to recovery of fluorides, particularly ethyl fluoride in a system in which there is alkylated an isoparaffin, for example, isobutane and/or isopentane with an olefin, e.g., ethylene, propylene and/or butylenes and/or amylenes, etc.

Reasonable variation and modification are possible within the scope of the foregoing disclosure, drawing and the appended claims to the invention the essence of which is that a lean hydrogen fluoride containing stream is used to extract ethyl fluoride from a liquid propane containing the same, as described, and also that the vent gases obtained from an overhead from a depropanizer, from which said liquid propane can also be obtained, is separately contacted with a lean HF stream thus permitting to obtain economically a propane yield stream substantially free from ethyl fluoride and a vent gas also substantially free from ethyl fluoride, also substantially as described.

I claim:

1. In the alkylation of an isoparaffin and an olefin in the presence of a catalyst and ethyl fluoride thereby obtaining an alkylate stream which is fractionated to produce an overhead comprising propane and ethyl fluoride, the method of:
  1. condensing said overhead thereby obtaining:
      a. a liquid stream comprising propane and ethyl fluoride, and
      b. a vent gas stream comprising propane and ethyl fluoride;
  2. contacting said liquid stream with a first lean hydrogen fluoride stream thereby removing ethyl fluoride into the hydrogen fluoride;
  3. recovering propane substantially free of ethyl fluoride from said liquid stream;
  4. contacting said vent gas with a second lean hydrogen fluoride stream thereby removing ethyl fluoride into the hydrogen fluoride;
  5. further treating the vent gas from step (4) with a liquid that will absorb hydrogen fluoride, said liquid chosen from among water, and mixtures comprising hydrogen fluoride with a preponderance of water;
  6. recovering a vent gas substantially free of ethyl fluoride and hydrogen fluoride.

2. A method of claim 1 further comprising passing said liquid from step (5) containing absorbed hydrogen fluoride into contact with olefins and hydrogen fluoride to form an admixture comprising alkyl fluorides suitable for use in an alkylation reaction.

3. A method according to claim 1 wherein the hydrogen fluoride streams into which ethyl fluoride has been removed are recycled for reuse in the alkylation.

4. A method of claim 1 wherein said absorbing liquid is water.

* * * * *